United States Patent [19]

Forsberg

[11] Patent Number: 5,041,598
[45] Date of Patent: * Aug. 20, 1991

[54] NITROGEN- AND PHOSPHORUS-CONTAINING COMPOSITIONS AND AQUEOUS SYSTEMS CONTAINING SAME

[75] Inventor: John W. Forsberg, Mentor-on-the-Lake, Ohio

[73] Assignee: The Lubrizol Corporation, Wickliffe, Ohio

[*] Notice: The portion of the term of this patent subsequent to Sep. 20, 2005 has been disclaimed.

[21] Appl. No.: 405,074

[22] Filed: Sep. 7, 1989

Related U.S. Application Data

[63] Continuation of Ser. No. 214,233, Jul. 1, 1988, abandoned, which is a continuation of Ser. No. 879,501, Jun. 25, 1986, Pat. No. 4,772,739, which is a continuation of Ser. No. 580,033, Feb. 14, 1984, abandoned.

[51] Int. Cl.$^5$ ................................................ C07F 9/02
[52] U.S. Cl. .................................... 558/208; 252/78.5
[58] Field of Search ........................ 558/208; 252/78.5

[56] References Cited

U.S. PATENT DOCUMENTS

| | | | |
|---|---|---|---|
| 2,737,492 | 3/1956 | Beegle et al. | 252/32.7 |
| 3,002,014 | 9/1961 | Dinsmore et al. | 558/208 |
| 3,058,910 | 10/1962 | Culmer | 252/32.7 |
| 3,074,990 | 1/1963 | Cyba | 558/208 |
| 3,133,787 | 5/1964 | Kelley | 21/2.7 |
| 3,184,412 | 5/1965 | Lowe et al. | 252/46.7 |
| 3,185,645 | 5/1965 | Clayton | 252/46.7 |
| 3,201,447 | 8/1965 | Cyba | 558/208 |
| 3,294,816 | 12/1966 | Latos et al. | 260/326 |
| 3,320,164 | 5/1967 | Brunnel | 252/49 |
| 3,359,347 | 12/1967 | Cyba | 558/208 |
| 3,396,109 | 9/1968 | Butler et al. | 252/32.7 |
| 3,484,374 | 12/1969 | Cyba | 252/32.7 |
| 3,484,504 | 12/1969 | Cyba | 558/208 |
| 3,502,677 | 3/1970 | Le Seur | 260/268 |
| 3,519,563 | 7/1970 | Lowe | 252/32.7 |
| 3,634,117 | 1/1972 | Wegerhoff et al. | 117/138.8 F |
| 3,826,745 | 7/1974 | Ryer et al. | 252/32.7 E |
| 3,926,821 | 12/1975 | Le Seur | 252/46.7 |
| 4,026,812 | 5/1977 | Le Seur | 252/75 |
| 4,085,054 | 4/1978 | Bussie et al. | 252/49.3 |
| 4,101,427 | 7/1978 | Shaub | 252/32.7 E |
| 4,154,779 | 5/1979 | Kreutzer | 558/208 |
| 4,160,089 | 7/1979 | Bussi et al. | 544/78 |
| 4,215,002 | 7/1980 | Fein | 252/32.5 |
| 4,234,435 | 11/1980 | Meinhardt et al. | 252/51.5 A |
| 4,257,902 | 3/1981 | Singer | 252/18 |
| 4,329,249 | 5/1982 | Forsberg | 252/34.7 |
| 4,368,133 | 1/1983 | Forsberg | 252/75 |
| 4,721,802 | 1/1988 | Forsberg | 558/207 |
| 4,772,739 | 9/1988 | Forsberg | 558/208 |

FOREIGN PATENT DOCUMENTS

| | | |
|---|---|---|
| 014288 | 8/1980 | European Pat. Off. . |
| 1009197 | 8/1962 | United Kingdom . |
| 1009914 | 11/1965 | United Kingdom . |
| 1044810 | 10/1966 | United Kingdom . |
| 1357745 | 6/1974 | United Kingdom . |
| 2083048 | 3/1982 | United Kingdom . |

OTHER PUBLICATIONS

Vipper et al., "Antifriction and Antiwear Efficiency of Ashless Thiophosphates and Dithiophosphates", in I. M. Gubkin Moscow Institute of the Petrochemical and Gas Industry, Mar. 1983.

Primary Examiner—Jose G. Dees
Assistant Examiner—Deborah D. Carr
Attorney, Agent, or Firm—Forrest L. Collins; Frederick D. Hunter; Robert A. Franks

[57] ABSTRACT

A composition comprising the reaction product of (A) at least one carboxylic acid acylating agent, (B) at least one amine characterized by the presence within its structure of at least one HN> group, and (C) at least one phosphorus-containing acid of the formula

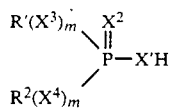

wherein each $X^1$, $X^2$, $X^3$ and $X^4$ is independently oxygen or sulfur, each m is zero or one, and each $R^1$ and $R^2$ is independently a hydrocarbyl group. Aqueous concentrates and water-based functional fluids comprising the foregoing composition are also disclosed.

46 Claims, No Drawings

NITROGEN- AND PHOSPHORUS-CONTAINING COMPOSITIONS AND AQUEOUS SYSTEMS CONTAINING SAME

This is a continuation of co-pending application Ser. No. 214,233 filed on July 1, 1988, now abandoned which is a continuation application of Ser. No. 06/879,501, filed 6/25/86, now U.S. Pat. No. 4,772,739 which is a continuation of Ser. No. 06/580,033, filed 2/14/84, now abandoned.

TECHNICAL FIELD

This invention relates to nitrogen- and phosphorus-containing compositions and aqueous systems containing such compositions. The nitrogen- and phosphorus-containing compositions are formed by reacting at least one carboxylic acid acylating agent, at least one amine and at least one phosphorus-containing acid. The aqueous systems encompass both aqueous concentrates and water-based functional fluids. The nitrogen- and phosphorus-containing compositions are useful as ashless anti-wear, E.P. (extreme pressure) and/or load-carrying agents for water-based functional fluids, and are characterized by significantly reduced toxicity levels.

BACKGROUND OF THE INVENTION

The term "water-based functional fluid" is used herein to refer to water-based lubricants, hydraulic fluids, cutting fluids and the like. Water-based functional fluids are not a new concept. However, in recent times, the increasing cost and scarcity of petroleum has made it increasingly desirable to replace oil-based functional fluids with water-based functional fluids wherever possible. Other benefits can also flow from such replacements such as decreased fire hazard and environmental pollution problems. In many cases, however, it is not feasible to make such replacements because the water-based functional fluids cannot be modified in their properties so as to perform to the same high degree as their oil-based counterparts. For example, it has been often difficult, if not impossible to replace certain oil-based hydraulic fluids with water-based fluids even though the desirability of doing so is evident.

Various E.P. agents, load-carrying and anti-wear agents have been proposed for use in water-based functional fluids. Most of these agents have, however, been found to be ineffective in imparting desired E.P., load-carrying or anti-wear properties, or have been found to be too toxic.

Carboxylic acid derivatives made from high molecular weight carboxylic acid acylating agents and amino compounds and their use in oil-based lubricants are known. See, for example, U.S. Pat. Nos. 3,216,936; 3,219,666; 3,502,677; and 3,708,522.

Phosphorus-containing and phosphorus- and sulfur-containing acids and their use in oil-based lubricants are also known. See, for example, U.S. Pat. No. 4,289,635.

It would be advantageous to provide improved ashless E.P., load-carrying and anti-wear agents suitable for use in water-based functional fluids. It would be particularly advantageous if these were satisfactorily non-toxic.

SUMMARY OF THE INVENTION

The present invention contemplates the provision of nitrogen- and phosphorus-containing compositions which are useful as ashless E.P., load-carrying and/or anti-wear agents in water-based functional fluids. These compositions are particularly advantageous due to the fact that they are relatively non-toxic.

Broadly stated, the present invention provides for a composition comprising the reaction product of (A) at least one carboxylic acid acylating agent, (B) at least one amine characterized by the presence within its structure of at least one HN< group, and (C) at least one phosphorus-containing acid of the formula

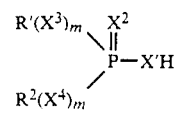

wherein each $X'$, $X^2$, $X^3$ and $X^4$ is independently oxygen or sulfur, each m is zero or one, and each $R'$ and $R^2$ is independently a hydrocarbyl group. Aqueous concentrates as well as water-based functional fluids such as water-based lubricants, hydraulic fluids, cutting fluids and the like comprising the foregoing composition are within the scope of the invention.

DESCRIPTION OF THE PREFERRED EMBODIMENTS

The term "hydrocarbyl" (and cognate terms such as hydrocarbyloxy, hydrocarbylmercapto, etc.) is used herein to include substantially hydrocarbyl groups (for example, substantially hydrocarbyloxy, substantially hydrocarbylmercapto, etc.), as well as purely hydrocarbyl groups. The description of these groups as being substantially hydrocarbyl means that they contain no non-hydrocarbyl substituents or non-carbon atoms which significantly affect the hydrocarbyl characteristics or properties of such groups relevant to their uses as described herein. For example, in the context of this invention, a purely hydrocarbyl $C_{40}$ alkyl group and a $C_{40}$ alkyl group substituted with a methoxy substituent are substantially similar in their properties with regard to their use in this invention and would be hydrocarbyl.

Non-limiting examples of substituents which do not significantly alter the hydrocarbyl characteristics or properties of the general nature of the hydrocarbyl groups of this invention are the following:

Ether groups (especially hydrocarbyloxy such as phenoxy, benzyloxy, methoxy, n-butoxy, etc., and particularly alkoxy groups of up to ten carbon atoms);

Oxo groups (e.g., —O— linkages in the main carbon chain);

Nitro groups;

Thioether groups (especially $C_{1-10}$ alkyl thioether);

Thia groups (e.g., —S— linkages in the main carbon chain);

Carbohydrocarbyloxy groups (e.g.,

hydrocarbyl);

Sulfonyl groups (e.g.,

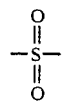

hydrocarbyl); and
Sulfinyl groups (e.g.,

hydrocarbyl).

This list is intended to be merely illustrative and not exhaustive, and the omission of a certain class of substituent is not meant to require its exclusion. In general, if such substituents are present, there will not be more than two for each ten carbon atoms in the substantially hydrocarbyl group and preferably not more than one for each ten carbon atoms since this number of substituents usually will not substantially affect the hydrocarbyl characteristics and properties of the group. Nevertheless, the hydrocarbyl groups usually will be free from non-hydrocarbon groups due to economic considerations; that is, they will be purely hydrocarbyl groups consisting of only carbon and hydrogen atoms.

The term "lower" as used in the present specification and claims, when used in conjunction with terms such as alkyl, alkenyl, alkoxy, and the like, is intended to describe such groups which contain a total of up to seven carbon atoms.

THE CARBOXYLIC ACID ACYLATING AGENTS, (A)

The carboxylic acid acylating agents (A) of the present invention can be one or more lower molecular weight carboxylic acid acylating agents of from one to about less than 18 carbon atoms, or one or more higher molecular weight hydrocarbyl-substituted carboxylic acid acylating agents, or a mixture of one or more lower molecular weight, and one or more higher molecular weight agents.

The lower molecular weight agents include the mono- or polycarboxylic acid acylating agents of one to about 18 carbon atoms such as fatty acids having 10 to about 18 carbon atoms or a tetrapropenyl-substituted succinic anhydride. Typical lower molecular weight monocarboxylic acylating agents include saturated and unsaturated fatty acids, such as lauric acid, stearic acid, oleic acid, myristic acid, linoleic acid, and the like. Anhydrides, when available, and lower alkyl esters of these acids can also be used. Mixtures of two or more such agents can also be used. An extensive discussion of such acids is found in Kirk-Othmer "Encyclopedia of Chemical Technology" 2nd Edition, 1965, John Wiley & Sons, N.Y., pp. 811-856. Acylating agents including acetic acid, propionic acid, butyric acid, acrylic and benzoic acid as well as their anhydrides and lower alkyl esters are also useful.

Among the useful lower molecular weight polycarboxylic acylating agents are maleic acid, fumaric acid, itaconic acid, mesaconic acid, succinic acid, phthalic acid, alkyl-substituted phthalic acids, isophthalic acid, malonic acid, glutaric acid, adipic acid, citraconic acid, glutaconic acid, chloromaleic acid, ataconic acid, scorbic acid, etc. Again anhydrides, when available, and lower alkyl esters and esters of these acids can be used as lower molecular weight acylating agents.

Certain substituted succinic acid and anhydride lower molecular weight acylating agents can also be used. A number of these are discussed in the above-cited Kirk-Othmer article at pp. 847-849. The typical such acylating agents can be represented by the formula:

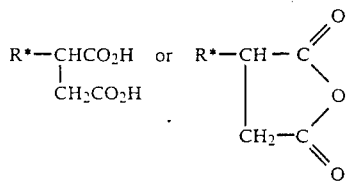

wherein R* is a $C_1$ to about a $C_{10}$ hydrocarbyl group. Preferably, R* is an aliphatic or alicyclic hydrocarbyl group less than 10% of its carbon-to-carbon bonds unsaturated. Examples of such groups are 4-butylcyclohexyl, di(isobutyl), decyl, etc. The production of such substituted succinic acids and their derivatives via alkylation of maleic acid or its derivatives with a halohydrocarbon is well known to those of skill in the art and need not be discussed in detail at this point.

Acid halides of the afore-described lower molecular weight mono- and polycarboxylic acids can be used as lower molecular weight acylating agents in this invention. These can be prepared by the reaction of such acids or their anhydrides with halogenating agents such as phosphorus tribromide, phosphorus pentachloride, phosphorus oxychloride, or thionyl chloride. Esters of such acids can be prepared simply by the reaction of the acid, acid halide or anhydride with an alcohol or phenolic compound. Particularly useful are the lower alkyl and alkenyl alcohols such as methanol, ethanol, allyl alcohol, propanol, cyclohexanol, etc. Esterification reactions are usually promoted by the use of alkaline catalysts such as sodium hydroxide or alkoxide, or an acidic catalyst such as sulfuric acid or toluene sulfonic acid.

The higher molecular weight hydrocarbyl-substituted carboxylic acylating agents are well known additives for oil-based lubricants and fuels, and intermediates for making such additives. See, for example, the following U.S. patents which are hereby incorporated by reference: U.S. Pat. Nos. 3,219,666; 3,254,025; 3,271,310; 3,272,743; 3,272,746; 3,278,550; 3,288,714; 3,307,928; 3,346,354; 3,373,111; 3,374,174; 3,381,022; and 3,394,179.

The higher molecular weight hydrocarbyl-substituted carboxylic acylating agents are substituted carboxylic acid acylating agents made by reacting one or more alpha-beta olefinically unsaturated carboxylic acid reagents containing on average from two to about 20 carbon atoms, exclusive of the carboxyl-based groups, with one or more olefin polymers or chlorinated analogs thereof.

The alpha-beta olefinically unsaturated carboxylic acid reagents may be either the acid per se or functional derivatives thereof, e.g., anhydrides, esters, acylated nitrogen, acyl halide, nitriles, metal salts. These carboxylic acid reagents may be either monobasic or polybasic in nature. When they are polybasic they are preferably dicarboxylic acids, although tri- and tetracarboxylic acids can be used. Exemplary of the monobasic alpha-beta olefinically unsaturated carboxylic acid reagents are the carboxylic acids corresponding to the formula:

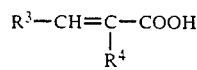

wherein $R^3$ is hydrogen, or a saturated aliphatic or alicyclic, aryl, alkylaryl or heterocyclic group, preferably hydrogen or a lower alkyl group, and $R^4$ is hydrogen or a lower alkyl group. The total number of carbon atoms in $R^3$ and $R^4$ should not exceed about 18 carbon atoms. Specific examples of useful monobasic alpha-beta olefinically unsaturated carboxylic acids are acrylic acid, methacrylic acid, cinnamic acid, crotonic acid, 3-phenyl propenoic acid, alpha, beta-decanoic acid, etc. Exemplary polybasic acids include maleic acid, fumaric acid, mesaconic acid, itaconic acid and citraconic acid.

The alpha-beta olefinically unsaturated carboxylic reagents can also be functional derivatives of the foregoing acids. These functional derivatives include the anhydrides, esters, acylated nitrogen, acid halides, nitriles and metal salts of the afore-described acids. A preferred alpha-beta olefinically unsaturated carboxylic acid reagent is maleic anhydride. Methods of preparing such functional derivatives are well known to those of ordinary skill in the art and they can be satisfactorily described by noting the reactants used to produce them. Thus, for example, derivative esters for use in the present invention can be made by esterifying monohydric or polyhydric alcohols or epoxides with any of the afore-described acids. Amines described hereinafter can be used to prepare these functional derivatives. The nitrile functional derivatives of the afore-described carboxylic acid useful in making the products of the present invention can be made by the conversion of a carboxylic acid to the corresponding nitrile by dehydration of the corresponding amide. The preparation of the latter is well known to those skilled in the art and is described in detail in *The Chemistry of the Cyano Group* edited by Zvi Rappoport, Chapter 2, which is hereby incorporated by reference for its relevant disclosures pertaining to methods for preparing nitriles.

Ammonium salt acylated nitrogen functional derivatives can also be made from any of the amines described hereinafter as well as from tertiary amino analogs of them (i.e., analogs wherein the —NH groups have been replaced with —N—hydrocarbyl or —N—hydroxy hydrocarbyl groups), ammonia or ammonium compounds (e.g., $NH_4Cl$, $NH_4OH$, etc.) by conventional techniques well known to those of ordinary skill in the art.

The metal salt functional derivatives of the foregoing carboxylic acid reagents can also be made by conventional techniques well known to those of ordinary skill in the art. Preferably they are made from a metal, mixture of metals, or a basically reacting metal derivative such as a metal salt or mixture of metal salts where the metal is chosen from Group Ia, Ib, IIa or IIb of the periodic table although metals from Groups IVa, IVb, Va, Vb, VIa, VIb, VIIb and VIII can also be used. The gegen ion (i.e., counter) of the metal salt can be inorganic such as halide, sulfide, oxide, carbonate, hydroxide, nitrate, sulfate, thiosulfate, phosphite, phosphate, etc., or organic such as lower alkanoic, sulfoate, alcoholate, etc. The salts formed from these metals and the acid products can be "acidic" or "normal" salts. An "acidic" salt is one in which the equivalents of acid exceed the stoichiometric amounts required to neutralize the number of equivalents of metal. A "normal" salt is one wherein the metal and acid are present in stoichiometrically equivalent amounts.

The acid halide functional derivative of the afore-described carboxylic acid reagents can be prepared by the reaction of the acids and their anhydrides with a halogenation agent such as phosphorus tribromide, phosphorus pentachloride or thionyl chloride. Esters can be prepared by the reaction of the acid halide with the aforesaid alcohols or phenolic compounds such as phenol, naphthol, octyl phenol, etc. Also, amides and imides and other acylated nitrogen derivatives can be prepared by reacting the acid halide with the above-described amino compounds. These esters and acylated nitrogen derivatives can be prepared from the acid halides by conventional techniques well known to those of ordinary skill in the art.

The hydrocarbyl-based substituents of the higher molecular weight carboxylic acid acylating agents may be derived from olefin polymers of chlorinated analogs thereof. These substituents have an average of at least about 12 carbon atoms, more preferably an average of at least about 18 carbon atoms, still more preferably an average of at least about 30 carbon atoms, and still more preferably an average of at least about 50 carbon atoms. In a particularly advantageous embodiment, these substituents have an average of from about 12 to about 500 carbon atoms, more preferably from about 18 to about 500 carbon atoms, still more preferably from about 30 to about 500 carbon atoms, and still more preferably from about 50 to about 500 carbon atoms.

The olefin monomers from which the olefin polymers are derived are polymerizable olefin monomers characterized by having one or more ethylenic unsaturated groups. They can be monoolefinic monomers such as ethylene, propylene, butene-1, isobutene and octene-1 or polyolefinic monomers (usually di-olefinic monomers such as butadiene-1,3 and isoprene). Usually these monomers are terminal olefins, that is, olefins characterized by the presence of the group $C=CH_2$. However, certain internal olefins can also serve as monomers (these are sometimes referred to as medial olefins). When such medial olefin monomers are used, they normally are employed in combination with terminal olefins to produce olefin polymers which are interpolymers. Although, hydrocarbyl-based substituents may also include aromatic groups (especially phenyl groups and lower alkyl and/or lower alkoxy-substituted phenyl groups such as para(tertiarybutyl)-phenyl groups) and alicyclic groups such as would be obtained from polymerizable cyclic olefins or alicyclic-substituted polymerizable cyclic olefins, the hydrocarbyl-based substituents are usually free from such groups. Nevertheless, olefin polymers derived from such interpolymers of both 1,3-dienes and styrenes such as butadiene-1,3 and styrene or para(tertiary butyl)styrene are exceptions to this general rule.

Generally the olefin polymers are homo- or interpolymers of terminal hydrocarbyl olefins of about two to about 30 carbon atoms, preferably about 2 to about 16 carbon atoms. A more typical class of olefin polymers is selected from that group consisting of homo- and interpolymers of terminal olefins of two to six carbon atoms, especially those of two to four carbon atoms.

Specific examples of terminal and medial olefin monomers which can be used to prepare the olefin polymers from which the hydrocarbyl-based substituents are derived include ethylene, propylene, butene-1, butene-2, isobutene, pentene-1, hexene-1, heptene-1, octene-1, nonene-1, decene-1, pentene-2, propylene tetramer, diisobutylene, isobutylene trimer, butadiene-1,2, butadiene-1,3, pentadiene-1,2, pentadiene-1,3, isoprene, hexadiene-1,5, 2-chlorobutadiene-1,3, 2-methylheptene-1, 3-cyclohexylbutene-1, 3,3-dimethylpentene-1, styrenedivinylbenzene, vinylacetate allyl alcohol, 1-methylvinylacetate, acrylonitrile, ethylacrylate, ethylvinylether and methylvinylketone. Of these, the purely hydrocarbyl monomers are more typical and the terminal olefin monomers are especially typical.

Often the olefin polymers are poly(isobutene)s such as obtained by polymerization of a $C_4$ refinery stream having a butene content of about 35 to about 75 percent by weight and an isobutene content of about 30 to about 60 percent by weight in the presence of a Lewis acid catalyst such as aluminum chloride or boron trifluoride. These polyisobutenes contain predominantly (that is, greater than about 80 percent of the total repeat units) isobutene repeat units of the configuration

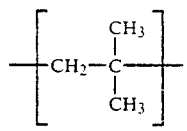

Typically, the hydrocarbyl-based substituent in the carboxylic acid acylating agent as used in the present invention is a hydrocarbyl, alkyl or alkenyl group.

Useful acylating agents include substituted succinic acid or anhydride agents containing hydrocarbyl-based substituents of about 12–500, more preferably about 18–500, still more preferably about 30–500 and still more preferably about 50–500 carbon atoms.

Often the components (A) of the present invention are substituted succinic acids or derivatives thereof which can be represented by the formula:

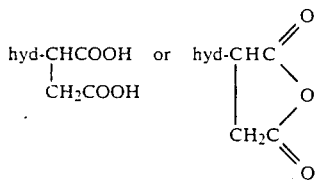

wherein "hyd" is the above-discussed hydrocarbyl-based substituent. Such succinic acid acylating agents can be made by the reaction of maleic anhydride, maleic acid, or fumaric acid with the afore-described olefin polymer, as is shown in the patents cited above. Generally, the reaction involves merely heating the two reactants at a temperature of about 150° to about 200°. Mixtures of the afore-said polymer olefins, as well as mixtures of unsaturated mono- and dicarboxylic acids can also be used.

THE AMINES, (B)

The amines (B) of this invention are characterized by the presence within their structure of at least one H—N< group, which can be a primary (i.e., —$NH_2$) or secondary (i.e., =NH) amino group. These amines can be monoamines or polyamines. Mixtures of two or more amines can be used.

The monoamines and polyamines useful in this invention can be aliphatic, cycloaliphatic, aromatic, or heterocyclic, including aliphatic-substituted aromatic, aliphatic-substituted cycloaliphatic, aliphatic-substituted heterocyclic, cycloaliphatic-substituted aliphatic, cycloaliphatic-substituted aromatic, cycloaliphatic-substituted heterocyclic, aromatic-substituted aliphatic, aromatic-substituted cycloaliphatic, aromatic-substituted heterocyclic, heterocyclic-substituted aliphatic, heterocyclic-substituted cycloaliphatic, and heterocyclic-substituted aromatic polyamines and may be saturated or unsaturated. If unsaturated, the amine is preferably free from acetylenic unsaturation (i.e., —C≡C). The polyamines may also contain non-hydrocarbon substituents or groups as long as these groups do not significantly interfere with the reaction of the polyamines with the acylating agents of this invention. Such non-hydrocarbon substituents or groups include lower alkoxy, lower alkyl mercapto, nitro, interrupting groups such as —O— and —S— (e.g., as in such groups as —$CH_2CH_2$—X—$CH_2CH_2$— where X is O or S).

With the exception of the branched polyalkylene polyamines, the polyoxyalkylene polyamines and the high molecular weight hydrocarbyl-substituted polyamines described more fully hereafter, the amines used in this invention ordinarily contain less than about 40 carbon atoms in total and often not more than about 20 carbon atoms in total.

Aliphatic monoamines include mono-aliphatic and di-aliphatic substituted amines wherein the aliphatic groups can be saturated or unsaturated and straight or branched chain. Thus, they are primary or secondary aliphatic amines. Such amines include, for example, mono- and di-alkyl-substituted amines, mono- and di-alkenyl-substituted amines, and amines having one N-alkenyl substituent and one N-alkyl substituent and the like. The total number of carbon atoms in these aliphatic monoamines preferably does not exceed about 40 and usually does not exceed about 20 carbon atoms. Specific examples of such monoamines include ethylamine, diethylamine, n-butylamine, di-n-butylamine, allylamine, isobutylamine, cocoamine, stearylamine, laurylamine, methyllaurylamine, oleylamine, N-methyl-octylamine, dodecylamine, octadecylamine, and the like. Examples of cycloaliphatic-substituted aliphatic amines, aromatic-substituted aliphatic amines, and heterocyclic-substituted aliphatic amines, include 2-(cyclohexyl)-ethylamine, benzylamine, phenylethylamine, and 3-(furylpropyl)amine.

Cycloaliphatic monoamines are those monoamines wherein there is one cycloaliphatic substitutent attached directly to the amino nitrogen through a carbon atom in the cyclic ring structure. Examples of such cycloaliphatic monoamines include cyclohexylamines, cyclopentylamines, cyclohexenylamines, cyclopentenylamine, N-ethyl-cyclohexylamine, dicyclohexylamines, and the like. Examples of such aliphatic-substituted, aromatic-substituted, and heterocyclic-substituted cycloaliphatic monoamines include propyl-substituted cyclohexylamines, phenyl-substituted cyclopentylamines, and pyranyl-substituted cyclohexylamine.

Aromatic monoamines include those monoamines wherein a carbon atom of the aromtic ring structure is attached directly to the amino nitrogen. The aromatic ring will usually be a mononuclear aromatic ring (i.e., one derived from benzene) but can include fused aromatic rings, especially those derived from naphthylene. Examples of such aromatic monoamines incude aniline, di(paramethylphenyl)amine, naphtylamine, N-(n-butyl)aniline, and the like. Examples of aliphatic-substituted, cycloaliphatic-substituted, and heterocyclic-substituted aromatic monoamines are para-ethoxyaniline, para-dodecylaniline, cyclohexyl-substituted naphthylamine, and thienyl-substituted aniline.

Suitable polyamines are aliphatic, cycloaliphatic and aromatic polyamines which are analogous to the monoamines described above except for the presence within their structure of another HN< group. The other amino nitrogen can be a primary, secondary or tertiary amino nitrogen. Examples of such polyamines include N-aminopropyl-cyclohexylamines, N-N'-di-n-butyl-para-phenylene diamine, bis-(para-aminophenyl)methane, 1,4-diaminocyclohexane, and the like.

The term "heterocyclic polyamine" is intended to describe those heterocyclic polyamines containing at least two primary or secondary amino groups and at least one nitrogen as a heteroatom in the heterocyclic ring. However, as long as there is present in the heterocyclic polyamines at least two primary or secondary amino groups, the hetero-N atom in the ring can be a tertiary amino nitrogen; that is, one that does not have hydrogen attached directly to the ring nitrogen. Heterocyclic polyamines can be saturated or unsaturated and can contain various substituents such as nitro, alkoxy, alkyl mercapto, alkyl, alkenyl, aryl, alkaryl, or aralkyl substituents. Generally, the total number of carbon atoms in the substituents will not exceed about 20. Heterocyclic polyamines can contain heteroatoms other than nitrogen, especially oxygen and sulfur. Obviously they can contain more than one nitrogen heteroatom. The 5- and 6-membered heterocyclic rings are preferred.

Among the suitable heterocyclics are aziridines, azetidines, azolidines, tetra- and di-hydro pyridines, pyrroles, indoles, piperadines, imidazoles, di- and tetrahydroimidazoles, piperazines, isoindoles, purines, morpholines, thiomorpholines, N-aminoalkylmorpholines, N-aminoalkylthiomorpholines, N-aminoalkylpiperazines, N,N'-di-aminoalkylpiperazines, azepines, azocines, azonines, azecines and tetra-, di- and perhydro-derivatives of each of the above and mixtures of two or more of these heterocyclic amines. Preferred heterocyclic amines are the saturated 5- and 6-membered heterocyclic amines containing only nitrogen, oxygen and/or sulfur in the hetero ring, especially the piperidines, piperazines, thiomorpholines, morpholines, pyrrolidines, and the like. Piperidine, aminoalkyl-substituted piperidines, piperazine, aminoalkyl-substituted piperazines, morpholine, aminoalkyl-substituted morpholines, pyrrolidine, and aminoalkyl-substituted pyrrolidines, are especially preferred. Usually the aminoalkyl substituents are substituted on a nitrogen atom forming part of the hetero ring. Specific examples of such heterocyclic amines include N-aminopropyl-morpholine, N-aminoethylpiperazine, and N,N'-di-aminoethylpiperazine.

Hydroxyamines, both mono- and polyamines, analogous to those amines described above are also useful in this invention provided they contain at least one primary or secondary amino group. The hydroxy-substituted amines contemplated are those having hydroxy substituents bonded directly to a carbon atom other than a carbonyl carbon atom; that is, they have hydroxy groups capable of functioning as alcohols. Examples of such hydroxy-substituted amines include ethanolamine, di-(3-hydroxypropyl)-amine, 3-hydroxybutyl-amine, 4-hydroxybutylamine, diethanolamine, di-(2-hydroxypropyl)-amine, N(hydroxypropyl)propylamine, N-(2-hydroxyethyl)-cyclohexylamine, 3-hydroxycyclopentylamine, para-hydroxyaniline, N-hydroxyethyl piperazine, and the like. The terms hydroxyamine and aminoalcohol describe the same class of compounds and, therefore, can be used interchangeably. Hereinafter, in the specification and appended claims, the term hydroxyamine will be understood to include aminoalcohols as well as hydroxyamines.

Also suitable as amines are the aminosulfonic acids and derivatives thereof corresponding to the formula:

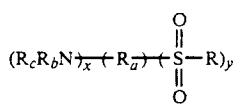

wherein R is —OH, —NH$_2$, ONH$_4$, etc., R$_a$ is a polyvalent organic radical having a valence equal to x+y; R$_b$ and R$_c$ are each independently hydrogen, hydrocarbyl, and substituted hydrocarbyl with the proviso that at least one of R$_b$ and R$_c$ is hydrogen per aminosulfonic acid molecule; x and y are each integers equal to or greater than one. From the formula, it is apparent that each aminosulfonic reactant is characterized by at least one HN< or H$_2$N— group and at least one

group. These sulfonic acids can be aliphatic, cycloaliphatic, or aromatic aminosulfonic acids and the corresponding functional derivatives of the sulfo group. Specifically, the aminosulfonic acids can be aromatic aminosulfonic acids, that is, where R$_a$ is a polyvalent aromatic radical such as phenylene where at least one

group is attached directly to a nuclear carbon atom of the aromatic radical. The aminosulfonic acid may also be a mono-amino aliphatic sulfonic acid; that is, an acid where x is one and R$_a$ is a polyvalent aliphatic radical such as ethylene, propylene, trimethylene, and 2-methylene propylene. Other suitable aminosulfonic acids and derivatives thereof useful as amines in this invention are disclosed in U.S. Pat. Nos. 3,926,820; 3,029,250; and 3,367,864; which are incorporated herein by reference.

Hydrazine and substituted-hydrazine can also be used as amines in this invention. Both nitrogens in the hydrazine must contain a hydrogen directly bonded thereto. The substituents which may be present on the hydrazine include alkyl, alkenyl, aryl, aralkyl, alkaryl, and the like. Usually, the substituents are alkyl, especially lower alkyl, phenyl, and substituted phenyl such as lower alkoxy-substituted phenyl or lower alkyl-substituted phenyl. Specific examples of substituted hydrazines are methylhydrazine, N,N'-dimethylhydrazine, phenylhydrazine, N-phenyl-N'-ethylhydrazine, N-(para-tolyl)-N'-(n-butyl)-hydrazine, N-(para-nitrophenyl)-hydrazine, N-(para-nitrophenyl)-N'-methylhydrazine, N,N'-di(para-chlorophenol)-hydrazine, N-phenyl-N'-cyclohexylhydrazine, and the like.

The high molecular weight hydrocarbyl polyamines, which can be used as polyamines in this invention are generally prepared by reacting a chlorinated polyolefin having a molecular weight of at least about 400 with a polyamine. Such polyamines are known and described, for example, in U.S. Pat. Nos. 3,275,554 and 3,438,757, both of which are expressly incorporated herein by reference for their disclosure in regard to how to prepare these amines. All that is required for use of these polyamines is that they possess at least two primary or secondary amino groups.

Another group of amines suitable for use in this invention are branched polyalkylene polyamines. The branched polyalkylene polyamines are polyalkylene polyamines wherein the branched group is a side chain containing on the average at least one nitrogen-bonded aminoalkylene

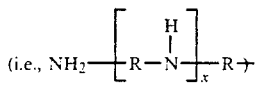

group per nine amino units present on the main chain, for example, 1–4 of such branched chains per nine units on the main chain, but preferably one side chain unit per nine main primary amino groups and at least one tertiary amino group.

These reagents may be expressed by the formula:

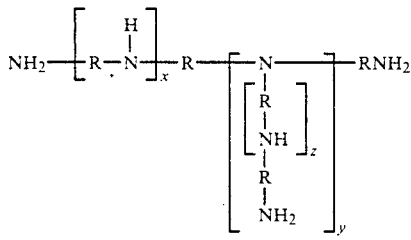

wherein R is an alkylene group such as ethylene, propylene, butylene and other homologs (both straight chained and branched), etc., but preferably ethylene; and x, y and z are integers, x being, for example, from 4 to 24 or more but preferably 6 to 18, y being, for example, 1 to 6 or more but preferably 1 to 3, and z being, for example, 0–6 but preferably 0–1. The x and y units may be sequential, alternative, orderly or randomly distributed.

A preferred class of such polyamines includes those of the formula

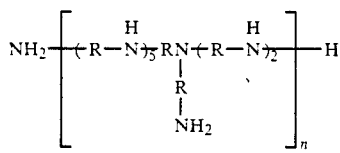

wherein n is an integer, for example, 1–20 or more but preferably 1–3, and R is preferably ethylene, but may be propylene, butylene, etc. (straight chained or branched).

Preferred embodiments are presented by the following formula:

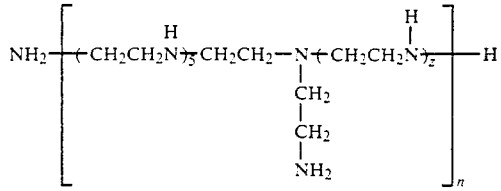

wherein n is an integer of from 1 to 3.

The groups in the brackets may be joined in a head-to-head or a head-to-tail fashion. Compounds described by this formula wherein n=1–3 are commercially available as Polyamines N-400, N-800, N-1200, etc. Polyamine N-400 has the above formula wherein n=1. U.S. Pat. Nos. 3,200,106 and 3,259,578 are incorporated herein by reference for their disclosure of how to make such polyamines and processes for reacting them with carboxylic acid acylating agents.

Suitable amines also include polyoxyalkylene polyamines, e.g., polyoxyalkylene diamines and polyoxyalkylene triamines, having average molecular weights ranging from about 200 to 4000 and preferably from about 400 to 2000. Illustrative examples of these polyoxyalkylene polyamines may be characterized by the formulae:

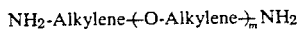

where m is an integer of about 3 to 70 and preferably about 10 to 35; and

wherein n is an integer of from about 3 to about 70 and generally from about 6 to about 35, and R is a polyvalent saturated hydrocarbyl group of up to about ten carbon atoms having a valence of 3 to 6. The alkylene groups may be straight or branched chains and contain from 1 to 7 carbon atoms, and usually from 1 to 4 carbon atoms. The various alkylene groups present within the above formulae may be the same or different.

More specific examples of these polyamines include:

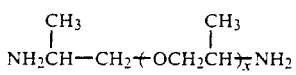

wherein x has a value of from about 3 to 70 and preferably from about 10 to 35 and

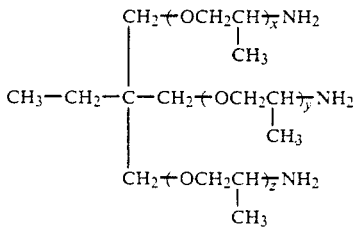

wherein $x+y+z$ have a total value ranging from about 3 to 30 and preferably from about 5 to 10.

Preferred polyoxyalkylene polyamines include the polyoxyethylene and polyoxypropylene diamines and the polyoxypropylene triamines having average molecular weights ranging from about 200 to 2000. The polyoxyalkylene polyamines are commercially available from, for example, the Jefferson Chemical Company, Inc. under the trade name "Jeff-amines D-230, D-400, D-1000, D-2000, T-403, etc.".

U.S. Pat. Nos. 3,804,763 and 3,948,800 are incorporated herein by reference for their disclosure of such polyoxyalkylene polyamines and process for acylating them with carboxylic acid acylating agents.

Preferred amines are the alkylene polyamines, including the polyalkylene polyamines, as described in more detail hereafter. The alkylene polyamines include those conforming to the formula

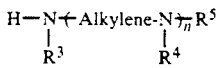

wherein n is from 1 to about 10; each $R^3$, $R^4$ and $R^5$ is independently a hydrogen atom, a hydrocarbyl group or a hydroxy-substituted hydrocarbyl group having up to about 40, preferably up to about 30, and advantageously from 1 to 10 carbon atoms; and the "Alkylene" group has from about 1 to about 10, preferably about 2 to about 6 carbon atoms and the particularly preferred alkylenes are ethylene and propylene. Especially preferred are the alkylene polyamines where each $R^3$, $R^4$ and $R^5$ is hydrogen with the ethylene polyamines and mixtures of ethylene polyamines being the most preferred. Usually n will have an average value of from about 2 to about 7. Such alkylene polyamines include methylene polyamines, ethylene polyamines, butylene polyamines, propylene polyamines, pentylene polyamines, hexylene polyamines, heptylene polyamines, etc. The higher homologs of such amines and related aminoalkyl-substituted piperazines are also included.

Alkylene polyamines useful in preparing the carboxylic derivative compositions include ethylene diamine, triethylene tetramine, propylene diamine, trimethylene diamine, hexamethylene diamine, decamethylene diamine, octamethylene diamine, di(heptamethylene)triamine, tripropylen tetramine, tetraethylene pentamine, trimethylene diamine, pentaethylene hexamine, di(trimethylene)triamine, N-(2-aminoethyl)piperazine, 1,4-bis(2-aminoethyl) piperazine, and the like. Higher homologs as are obtained by condensing two or more of the above-illustrated alkylene amines are useful as amines in this invention as are mixtures of two or more of any of the afore-described polyamines.

Ethylene polyamines, such as those mentioned above, are especially useful for reasons of cost and effectiveness. Such polyamines are described in detail under the heading "Diamines and Higher Amines" in The Encyclopedia of Chemical Technology, Second Edition, Kirk and Othmer, Volume 7, pages 27–39, Interscience Publishers, Division of John Wiley and Sons, 1965, which is hereby incorporated by reference for their disclosure of useful polyamines. Such compounds are prepared most conveniently by the reaction of an alkylene chloride with ammonia or by reaction of an ethylene imine with a ring-opening reagent such as ammonia, etc. These reactions result in the production of the somewhat complex mixtures of alkylene polyamines, including cyclic condensation products such as piperazines.

Hydroxyalkyl alkylene polyamines having one or more hydroxyalkyl substituents on the nitrogen atoms, and also useful in preparing compositions of the present invention. Preferred hydroxyalkyl-substituted alkylene polyamines are those in which the hydroxyalkyl group is a lower hydroxyalkyl group, i.e., having less than 8 carbon atoms. Examples of such hydroxyalkyl-substituted polyamines include N-(2-hydroxyethyl)ethylene diamine, N,N-bis(2-hydroxyethyl)ethylene diamine, 1-(2-hydroxyethyl)piperazine, monohydroxypropyl-substituted diethylene triamine, dihydroxypropyl-substituted tetraethylene pentamine, N-(3-hydroxybutyl)tetramethylene diamine, etc. Higher homologs as are obtained by condensation of the above-illustrated hydroxy alkylene polyamines through amino radicals or through hydroxy radicals are likewise useful as amines in this invention. Condensation through amino radicals results in a higher amine accompanied by removal of ammonia and condensation through the hydroxy radicals results in products containing ether linkages accompanied by removal of water.

THE PHOSPHORUS-CONTAINING ACIDS, (C)

The phosphorus-containing acids (C) of the present invention, can be represented by the general formula

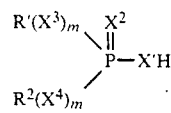

wherein each $X^1$, $X^2$, $X^3$ and $X^4$ is independently oxygen or sulfur, each m is zero or one, and each $R^1$ and $R^2$ is independently a hydrocarbyl-based group. Illustrative examples of some preferred phosphorus-containing acids are:

1. Dihydrocarbyl phosphinodithioic acids corresponding to the formula

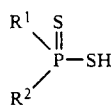

2. S-hydrocarbyl hydrocarbyl phosphonotrithioic acids corresponding to the formula

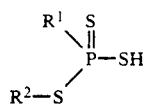

3. O-hydrocarbyl hydrocarbyl phosphonodithioic acids corresponding to the formula

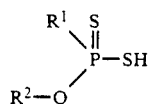

4. S,S-dihydrocarbyl phosphorotetrathioic acids corresponding to the formula

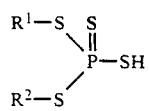

5. O,S-dihydrocarbyl phosphorotrithioic acids corresponding to the formula

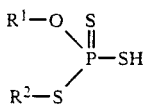

6. O,O-dihydrocarbyl phosphorodithioic acids corresponding to the formula

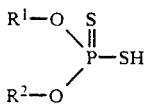

Preferred acids of the formula

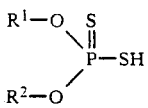

are readily obtainable by the reaction of phosphorus pentasulfide ($P_2S_5$) and an alcohol or a phenol. The reaction involves mixing at a temperature of about 20° to about 200° C., four moles of alcohol or a phenol with one mole of phosphorus pentasulfide. Hydrogen sulfide is liberated in this reaction. The oxygen-containing analogs of these acids are conveniently prepared by treating the dithioic acid with water or stream which, in effect, replaces one or both of the sulfur atoms.

Preferred phosphorus-containing acids are phosphorus- and sulfur-containing acids. These preferred acids preferably include those acids wherein at least one $X'$ or $X^2$ is sulfur, and more preferably both $X'$ and $X^2$ are sulfur, at least one $X^3$ or $X^4$ is oxygen or sulfur, more preferably both $X^3$ and $X^4$ are oxygen and m is 1. Mixtures of these acids may be employed in accordance with this invention.

Each $R'$ and $R^2$ is independently a hydrocarbyl-based group that is preferably free from acetylenic and usually also from ethylenic unsaturation and have from about 1 to about 50 carbon atoms, preferably from about 1 to about 30 carbon atoms, and more preferably from about 3 to about 18 carbon atoms. In a particularly advantageous embodiment each $R'$ and $R^2$ is the same or different and has from about 4 to about 8 carbon atoms. Each $R'$ and $R^2$ can be, for example, isopropyl, isobutyl, 4-methyl-2-pentyl, 2-ethylhexyl, iso-octyl, etc. Each $R'$ and $R^2$ can be identical to each other, although they may be different and either or both may be mixtures. Each $R'$ and $R^2$ is preferably alkyl, and most desirably branched alkyl.

PROCESS FOR MAKING THE NITROGEN- AND PHOSPHORUS-CONTAINING COMPOSITIONS

The process of this invention may be carried out by mixing the components (A), (B) and (C) in any order. All three reactants may be mixed at room temperature and heated to a temperature above about 80° C. to effect acylation. The reaction may likewise be carried out by first reacting components (B) and (C) and then acylating the intermediate product with component (A), or by acylating the component (B) with component (A) and then reacting the acylated amine with component (C). This last mentioned mode of carrying out the process is preferred because the products obtained have been found to be especially useful for the purpose of this invention. The preferred temperature for carrying out the acylation is between about 100° C. to about 300° C., preferably about 150° C. and 250° C.

The acylation is accompanied by the formation of water. The removal of the water formed can be effected by heating the reaction mixture to 100° C. or higher. It may be facilitated by blowing the reaction mixture with an inert gas such as nitrogen during such heating. It may be facilitated also by the use in the reaction mixture of an inert solvent which forms a co-distillable azeotropic mixture with water. Examples of such solvents are benzene, n-hexane, toluene, xylene, etc. The use of such solvents permits the removal of water at a substantially lower temperatuare, e.g., 80° C.

The relative proportions of reactants to be used in the process are based upon the stoichiometry of the reaction involved in the process and the utility of the products obtained therefrom for the purpose of this invention. The minimum amounts of components (A) and (C) to be used are about 0.5 equivalent of each of said components (A) and (C) for each mole of component (B). The maximum amounts of components (A) and (C) to be used are based on the total number of equivalents of component (B) used.

For purposes of this invention the number of equivalents of a amine (B) is based on the number of $HN<$ groups in such amine. An equivalent weight of an amine is the total weight of amine divided by the total number of $HN<$ groups present. Thus, ethylene diamine has an equivalent weight equal to one-half its molecular weight; and tetraethylene pentamine has an equivalent weight equal to one-fifth its molecular weight. Also, for example, the equivalent weight of a commercially available mixture of amines can be determined by dividing the atomic weight of nitrogen (14) by the weight percent of nitrogen contained in the amine. Therefore, an amine mixture having a % N of 34 would have an equivalent weight of 41.2. The number of equivalents of an amine can be determined by dividing its total weight by its equivalent weight.

The number of equivalents of acylating agent (A) depends on the number of carboxylic functions (e.g., carboxylic acid groups or functional derivatives thereof) present in the acylating agent. Thus, the number of equivalents of acylating agents will vary with the number of carboxy groups present therein. In determining the number of equivalents of acylating agents, those carboxyl functions which are not capable of reacting as a carboxylic acid acylating agent are excluded. In general, however, there is one equivalent of acylating agent for each carboxy group in the acylating agents. For example, there would be two equivalents in the acylating agents derived from the reaction of one mole of olefin polymer and one mole of maleic anhydride. Conventional techniques are readily available for determining the number of carboxyl functions (e.g., acid number, saponification number) and, thus, the number of equivalents of acylating agent available to react with amine.

The equivalent weight of component (C) can be determined by dividing the molecular weight of component (C) by the number of —PXXH groups. These can usually be determined from the structural formula of component (C) or empirically through well known titration procedures. The number of equivalents of component (C) can be determined by dividing the weight of component (C) by its equivalent weight.

The maximum combined equivalents of components (A) and (C) which can react with one mole of component (B) is equal to the number of HN< groups. If an excess of components (A) and (C) is used, this excess will not take part in the reaction and consequently such excess has little beneficial effect. On the other hand, if the total amount of components (A) and (C) used is less than the maximum amount, the products will contain unreacted free amino nitrogen atoms. Such products have been found to be useful in this invention. It has also been found that the products having particular usefulness in this invention are those obtained by the use of components (A) and (C) in relative amounts within the limits of ratio of equivalents from about 0.5:4.5 to about 4.5:0.5. A specific example illustrating the limits of the relative proportions of the reactants is as follows: one mole of a tetraalkylene pentamine is reacted with from about 0.5 to about 4.5 equivalents of a polyisobutene-substituted succinic anhydride and from about 0.5 to about 4.5 equivalents of a phosphorodithioic acid.

The following examples are illustrative of the preparation of the nitrogen- and phosphorus-containing compositions of the present invention. In the following examples, unless otherwise indicated, all parts and percentages are by weight.

EXAMPLE 1

1100 parts (2 equivalents) of polyisobutenyl (950 mol. wt.) substituted succinic anhydride are heated to 50° C. with stirring. 442 parts (10 equivalents) of tetraethylene pentamine are added to the polyisobutenyl-substituted succinic anhydride. An exotherm increases the temperature of the mixture to 80° C. The mixture is heated from 80° C. to 200° C. with a nitrogen purge at a rate of 1.0 standard cubic feet per hour over a 1.5-hour period. 200 parts diluent oil are added to the mixture to reduce foaming. The mixture is held at 200°-212° C. for five hours. 28 parts of aqueous distillate and 19 parts non-aqueous distillate are stripped from the mixture. The mixture is cooled to room temperature to provide the desired carboxylic acid derivative. The product is a medium viscosity fluid that is pourable at room temperature. The product has a nitrogen content of 8.47% and contains 11.6% diluent oil.

EXAMPLE 2

862 parts (4.556 equivalents) of the product of Example 1 are heated to 50° C. 1452 parts (3.523 equivalents) of O,O-di-(isooctyl) phosphorodithioic acid are added to the product of Example 1 dropwise over a period of 1.5 hours. An exotherm increases the temperature of the mixture to 70° C. The mixture is stirred for one hour at 65°-68° C. to provide the desired nitrogen- and phosphorus-containing composition. This product is a viscous (pours slowly at room temperature) dark brown fluid which has a sulfur content of 10.48%, a phosphorus content of 5.34% and a nitrogen content of 3.09%.

EXAMPLE 3

1100 parts (2 equivalents) of polyisobutenyl (950 mol. wt.) substituted succinic anhydride are heated to 50° C. with stirring. 221 parts (5 equivalents) of tetraethylene pentamine are added to the polyisobutenyl-substituted succinic anhydride. An exotherm increases the temperature of the mixture to 80° C. The mixture is heated from 80° C. to 200° C. with a nitrogen purge at a rate of 1.0 standard cubic feet per hour for a 1.5-hour period. 200 parts diluent oil are added to the mixture to reduce foaming. The mixture is held at 200°-218° C. for five hours. 23 parts of aqueous distillate and 19 parts non-aqueous distillate are stripped from the mixture. The mixture is cooled to room temperature to provide the desired carboxylic acid derivative. The product is a brown-green viscous fluid. The product has a nitrogen content of 4.76% and contains 13% diluent oil.

EXAMPLE 4

800 parts (2.1 equivalents) of the product of Example 3 are heated to 50° C. with stirring. 672 parts (1.63 equivalents) of O,O-di-(isooctyl) phosphordithioic acid are added dropwise over a period of one hour. An exotherm increases the temperature of the mixture from 50° to 70° C. The mixture is stirred for one hour at 70°-75° C. to provide the desired nitrogen- and phosphorus-containing composition. This product has a grease-like consistency and a black to dark brown color. This product has a nitrogen content 2.41%, a phosphorus content of 3.57%, a sulfur content of 7.73%, and contains 10% diluent oil.

EXAMPLE 5

1337 parts (2.43 equivalents) of polyisobutenyl (950 mol. wt.) substituted succinic anhydride are heated to 64° C. with stirring. 269 parts (6.075 equivalents) of tetraethylene pentamine are added to the polyisobutenyl substituted succinic anhydride over a period of 1-2 minutes. An exotherm increases the temperature of the mixture to 89° C. 243 parts diluent oil are added to the mixture to reduce foaming. The mixture is heated to 200° C. over a period of 1.5 hours. The mixture is maintained at a temperature of 200°-208° C. for five hours stripping off 12 parts of an aqueous distillate and 25 parts of a non-aqueous distillate. The mixture is cooled to room temperature. 25 parts (0.57 equivalent) of tetraethylene pentamine are added to the mixture. The resulting product is the desired carboxylic acid derivative. This product is a viscous fluid that is brown-green in color and has a diluent oil content of 13%.

EXAMPLE 6

1837 parts (4.82 equivalents) of the product of Example 5 are heated to 48° C. with stirring. 1522 parts (3.72 equivalents) of O,O-di-(isooctyl) phosphorodithioic acid are added dropwise to the mixture over a three-hour period while maintaining the temperature of the mixture at 50°-70° C. The mixture is stirred for one hour to provide the desired nitrogen- and phosphorus-containing composition. This product is a brown viscous fluid which as a nitrogen content of 2.93%, a phosphorus content of 3.55% and a sulfur content of 7.60%.

EXAMPLE 7

1455 parts (2.65 equivalents) of polyisobutenyl (950 mol. wt.) substituted succinic anhydride and 265 parts diluent oil are mixed together for 5-10 minutes. 585 parts (13.25 equivalents) of tetraethylene pentamine are added to the mixture dropwise over a period of 1-1.25 hours. An exotherm increases the temperature of the mixture to 90° C. The mixture is heated from 90° C. to 199° C. over a two-hour period stripping of 29 parts water. The mixture is cooled to room temperature to provide the desired carboxylic acid derivative which is a black viscous fluid containing 11.6% diluent oil.

EXAMPLE 8

1390 parts (6.6 equivalents) of the product of Example 7 are stirred at room temperature. 2051 parts (5 equivalents) of O,O-di-(isooctyl) phosphorodithioic acid are added to the product of Example 7 dropwise over a period of four hours. An exotherm increases the temperature of the mixture from room temperature to 60° C. after one hour. The mixture is maintained at 60°–70° C. for the next three hours of the addition. The mixture is stirred for one hour with the temperature cooling from 68° C. to 55° C. The resulting product is the desired nitrogen- and phosphorus-containing composition. This product is a black viscous fluid containing 3.56% nitrogen, 4.57% phosphorus, 9.98% sulfur, and 4.7% diluent oil.

EXAMPLE 9

876 parts (3 equivalents) of Unitol DSR-90, a product of Union Camp identified as a tall oil acid, are stirred at room temperature. 314 parts (7.51 equivalents) of tetraethylene pentamine are added to the mixture. An exotherm increases the temperature of the mixture from 22° C. to 68° C. The mixture is heated from 68° C. to 192° C. over a five-hour period with a nitrogen purge at a rate of 0.5 standard cubic feet per hour. Aqueous distillate is removed from the mixture. The mixture is cooled to 24° C. 1612 parts (3.94 equivalents) of O,O-di-(isooctyl)phosphorodithioic acid are added to the mixture in a fine stream over a period of one hour and 17 minutes. An exotherm increases the temperature of the mixture from 24° C. to 62° C. The mixture is stirred for 30 minutes to provide the desired nitrogen- and phosphorus-containing composition. The composition is a viscous fluid that is pourable at room temperature and has a nitrogen content of 3.84% by weight, a sulfur content of 10.09% by weight, and a phosphorus content of 4.54% by weight.

The terms "dispersed" and "dissolved" (and cognate terms such as "dispersion", "solution", etc.) are used throughout this specification and in the appended claims to refer to the distribution of the compositions of the invention in the aqueous systems to which they are added. While the practice of the present invention is not dependent on any particular theory or hypothesis to explain the invention, it should be understood that in some instances, the compositions of the invention may dissolve in the aqueous phase to form true solutions while in other instances, micelle dispersions or microemulsions may be formed which visibly appear to be true solutions. Whether a solution, micelle dispersion, or microemulsion is formed, is dependent on the particular composition employed and the particular system to which it is added. In any event, the terms "dispersed" and "dissolved" are used interchangeably throughout this specification and in the appended claims to refer to solutions, micelle dispersions, microemulsions and the like.

The invention includes aqueous systems characterized by a continuous aqueous phase with the nitrogen- and phosphorus-containing compositions of the present invention dispersed in said continuous aqueous phase. Preferably, these aqueous systems containing at least about 25% by weight water. Such aqueous systems encompass both concentrates containing about 25% to about 70%, preferably about 40% to about 70% water; and water-based functional fluids containing a major amount of water and a minor E.P. anti-wear and/or load-carrying amount of the compositions of the invention, preferably from about 0.05 to about 15%, more preferably about 0.1 to about 10%, and advantageously about 0.1 to about 5% by weight of the compositions of the invention. The concentrates generally contain less than about 50%, preferably less than about 25%, more preferably less than about 15%, and still more preferably less than about 6% hydrocarbyl oil. The water-based functional fluids contain less than about 15%, preferably less than about 5%, and more preferably less than about 2% hydrocarbyl oil. These concentrates and water-based functional fluids can optionally include other conventional additives commonly employed in water-based functional fluids. These other additives include dispersant/solubilizers, surfactants, functional additives, corrosion-inhibitors, shear stabilizing agents, bactericides, dyes, water-softeners, odor masking agents, anti-foam agents, and the like.

The concentrates are analogous to the water-based functional fluids except that they contain less water (i.e., less than about 70%) and proportionately more of the other ingredients. The concentrates can be converted to water-based functional fluids by dilution with water. This dilution is usually done by standard mixing techniques. This is often a convenient procedure since the concentrate can be shipped to the point of use before additional water is added. Thus, the cost of shipping a substantial amount of the water in the final water-based functional fluid is saved. Only the water necessary to formulate the concentrate (which is determined primarily by ease of handling and convenience factors), need be shipped.

Generally these water-based functional fluids are made by diluting the concentrates with water, wherein the ratio of water to concentrate is in the range of about 80:20 to about 99:1 by weight. As can be seen when dilution is carried out within these ranges, the final water-based functional fluid contains, at most, an insignificant amount of hydrocarbyl oil. This clearly distinguishes them from soluble oils.

Also included within the invention are methods for preparing aqueous systems, including both concentrates and water-based functional fluids, containing other conventional additives commonly employed in water-based functional fluids. These methods comprise the steps of:

(1) mixing the composition of the invention with such other conventional additives either simultaneously or sequentially to form a dispersion or solution; optionally (2) combining said dispersion or solution with water to form said aqueous concentrate; and/or (3) diluting said dispersion or solution, or concentrate with water wherein the total amount of water used is in the amount required to provide the desired concentration of the composition of the invention and other functional additives in said concentrates or said water-based functional fluids.

These mixing steps are carried out using conventional equipment and generally at room or slightly elevated temperatures, usually below 100° C. and often below 50° C. As noted above, the concentrate can be formed and then shipped to the point of use where it is diluted with water to form the desired water-based functional fluid. In other instances the finished water-based functional fluid can be formed directly in the same equipment used to form the concentrate or the dispersion or solution.

The dispersant/solubilizers that are useful in accordance with the present invention include the nitrogen-containing, phosphorus-free carboxylic solubilizers disclosed in U.S. Pat. Nos. 4,329,249 and 4,368,133. These patents are incorporated herein by reference. Briefly, these dispersant/solubilizers are made by reacting (I) at least one carboxylic acid acylating agent having at one hydrocarbyl-based substituent of at least about 12 to about 500 carbon atoms with (II) at least one (a) N-(hydroxyl-substituted hydrocarbyl) amine, (b) hydroxyl-substituted poly(hydrocarbyloxy) analog of said amine (a), or (c) mixtures of (a) and (b). Preferred acylating agents include the substituted succinic acids or anhydrides. Preferred amines include the primary, secondary and tertiary alkanol amines or mixtures thereof. These dispersant/solubilizers are preferably used at effective levels to disperse or dissolve the various additives, particularly the functional additives discussed below, in the concentrates and/or water-based functional fluids of the present invention. In a particularly preferred embodiment of the present invention, the dispersant/solubilizer is the reaction product of a polyisobutenyl-substituted succinic anhydride with a mixture of diethylethanolamine and ethanolamine.

The surfactants that are useful can be of the cationic, anionic, nonionic or amphoteric type. Many such surfactants of each type are known to the art. See, for example, McCutcheon's "Emulsifiers & Detergents", 1981, North American Edition, published by McCutcheon Division, MC Publishing Co., Glen Rock, N.J., U.S.A., which is hereby incorporated by reference for its disclosures in this regard.

Among the nonionic surfactant types are the alkylene oxide-treated products, such as ethylene oxide-treated phenols, alcohols, esters, amines and amides. Ethylene oxide/propylene oxide block copolymers are also useful nonionic surfactants. Glycerol esters and sugar esters are also known to be nonionic surfactants. A typical nonionic surfactant class useful with the present invention are the alkylene oxide-treated alkyl phenols such as the ethylene oxide alkyl phenol condensates sold by the Rohm & Haas Company. A specific example of these is Triton X-100 which contains an average of 9-10 ethylene oxide units per molecule, has an HLB value of about 13.5 and a molecular weight of about 628. Many other suitable nonionic surfactants are known; see, for example, the aforementioned McCutcheon's as well as the treatise "Non-ionic Surfactants" edited by Martin J. Schick, M. Dekker Co., New York, 1967, which is hereby incorporated by reference for its disclosures in this regard.

As noted above, cationic, anionic and amphoteric surfactants can also be used. Generally, these are all hydrophilic surfactants. Anionic surfactants contain negatively charged polar groups while cationic surfactants contain positively charged polar groups. Amphoteric dispersants contain both types of polar groups in the same molecule. A general survey of useful surfactants is found in Kirk-Othmer Encyclopedia of Chemical Technology, Second Edition, Volume 19, page 507 et seq. (1969, John Wiley and Son, New York) and the aforementioned compilation published under the name of McCutcheon's. These references are both hereby incorporated by reference for their disclosures relating to cationic, amphoteric and anionic surfactants.

Among the useful anionic surfactant types are the widely known carboxylate soaps, organo sulfates, sulfonates, sulfocarboxylic acids and their salts, and phosphates. Useful cationic surfactants include nitrogen compounds such as amine oxides and the well-known quaternary ammonium salts. Amphoteric surfactants include amino acid-type materials and similar types. Various cationic, anionic and amphoteric dispersants are available from the industry, particularly from such companies as Rohm & Haas and Union Carbide Corporation, both of America. Further information about anionic and cationic surfactants also can be found in the texts "Anionic Surfactants", Parts II and III, edited by W. M. Linfield, published by Marcel Dekker, Inc., New York, 1976 and "Cationic Surfactants", edited by E. Jungermann, Marcel Dekker, Inc., New York, 1976. Both of these references are incorporated by reference for their disclosures in this regard.

These surfactants, when used, are generally employed in effective amounts to reduce the viscosity of aqueous systems of the invention and/or aid in the dispersal of the various additives, particularly the functional additives discussed below, in such systems.

While the compositions of the present invention are useful as E.P., anti-wear and load-carrying agents, the use of additional functional additives to supplement the activity of these compositions may be desirable. These additional functional additives are typically oil-soluble, water-insoluble additives which function in conventional oil-based systems as E.P. agents, anti-wear agents, load-carrying agents, friction modifiers, and/or lubricity agents. They can also function as anti-slip agents, film formers, friction modifiers and/or lubricity agents. As is well known, such additives can function in two or more of the above-mentioned ways; for example, E.P. agents often function as load-carrying agents.

The term "oil-soluble, water-insoluble functional additive" refers to a functional additive which is not soluble in water above a level of about 1 gram per 100 milliliters of water at 25°, but is soluble in mineral oil to the extent of at least one gram per liter at 25°.

These functional additives can also include certain solid lubricants such as graphite, molybdenum disulfide and polytetrafluoroethylene and related solid polymers.

These functional additives can also include frictional polymer formers. Briefly, these are potential polymer forming materials which are dispersed in a liquid carrier at low concentration and which polymerize at rubbing or contacting surfaces to form protective polymeric films on the surfaces. The polymerizations are believed to result from the heat generated by the rubbing and, possibly, from catalytic and/or chemical action of the freshly exposed surface. A specific example of such materials is dilinoleic acid and ethylene glycol combinations which can form a polyester frictional polymer film. These materials are known to the art and descriptions of them are found, for example, in the journal "Wear", Volume 26, pages 369-392, and West German Published Patent Application 2,339,065. These disclosures are hereby incorporated by reference for their discussions of frictional polymer formers.

Typically these functional additives are known metal or amine salts of organo sulfur, phosphorus, boron or carboxylic acids which are the same as or of the same type as used in oil-based fluids. Typically such salts are of carboxylic acids of 1 to 22 carbon atoms including both aromatic and aliphatic acids; sulfur acids such as alkyl and aromatic sulfonic acids and the like; phosphorus acids such as phosphoric acid, phosphorus acid, phosphinic acid, acid phosphate esters and analogous sulfur homologs such as the thiophosphoric and dithiophosphoric acid and related acid esters; boron acids include boric acid, acid borates and the like. Useful functional additives also include metal dithiocarbamates such as molybdenum and antimony dithiocarbamates; as well as dibutyl tin sulfide, tributyl tin oxide, phosphates and phosphites; borate amine salts, chlorinated waxes;

trialkyl tin oxide, molybdenum phosphates, and chlorinated waxes.

Mainly such functional additives are known to the art. For example, descriptions of additives useful in conventional oil-based systems and in the aqueous systems of this invention are found in "Advances in Petroleum Chemistry and Refining," Volume 8, Edited by John J. McKetta, Interscience Publishers, New York, 1963, pages 31-38 inclusive; Kirk-Othmer "Encyclopedia of Chemical Technology," Volume 12, Second Edition, Interscience Publishers, New York, 1967, page 575 et seq.; "Lubricant Additives" by M. W. Ranney, Noyes Data Corporation, Park Ridge, N.J., U.S.A., 1973; and "Lubricant Additives" by C. V. Smalheer and R. K. Smith, The Lezius-Hiles Co., Cleveland, Ohio, U.S.A. These references are hereby incorporated by reference for their disclosures of functional additives useful in the systems of this invention.

In certain of the typical aqueous systems of the invention, the functional additive is a sulfur or chloro-sulfur E.P. agent, known to be useful in oil-base systems. Such materials include chlorinated aliphatic hydrocarbons, such as chlorinated wax; organic sulfides and polysulfides, such as benzyldisulfide, bis-(chlorobenzyl)disulfide, dibutyl tetrasulfide, sulfurized sperm oil, sulfurized methyl ester of oleic acid, sulfurized alkylphenol, sulfurized dipentene, sulfurized terpene, and sulfurized Diels-Alder adducts; phosphosulfurized hydrocarbons, such as the reaction product of phosphorus sulfide with turpentine or methyl oleate; phosphorus esters such as the dihydrocarbon and trihydrocarbon phosphites, i.e., dibutyl phosphite, diheptyl phosphite, dicyclohexyl phosphite, pentylphenyl phosphite, dipentylphenyl phosphite, tridecyl phosphite, distearyl phosphite and polypropylene substituted phenol phosphite; metal thiocarbamates, such as zinc dioctyldithiocarbamate and barium heptylphenol dithiocarbamate; and Group II metal salts of phosphorodithioic acid, such as zinc dicyclohexyl phosphorodithioate, and the zinc salts of a phosphorodithioic acid.

The functional additive can also be a film former such as a synthetic or natural latex or emulsion thereof in water. Such latexes include natural rubber latexes and polystyrene butadienes synthetic latex.

The functional additive can also be an anti-chatter or anti-squawk agent. Examples of the former are the amide metal dithiophosphate combinations such as disclosed in West German Patent No. 1,109,302; amine salt-azomethene combinations such as disclosed in British Patent Specification No. 893,977; or amine dithiophosphate such as disclosed in U.S. Pat. No. 3,002,014. Examples of anti-squawk agents are N-acylsarcosines and derivatives thereof such as disclosed in U.S. Pat. Nos. 3,156,652 and 3,156,653; sulfurized fatty acids and esters thereof such as disclosed in U.S. Pat. Nos. 2,913,415 and 2,982,734; and esters of dimerized fatty acids such as disclosed in U.S. Pat. No. 3,039,967. The above-cited patents are incorporated hereby by reference for their disclosure as pertinent to anti-chatter and anti-squawk agents useful as a functional additive in the aqueous systems of the present invention.

Specific examples of functional additives useful in the aqueous systems of this invention include the following commercially available products.

TABLE I

| Functional Additive Tradename | Chemical Description | Supplier |
|---|---|---|
| Anglamol 32 | Chlorosulfurized hydrocarbon | Lubrizol[1] |
| Anglamol 75 | Zinc dialkyl phosphate | Lubrizol[1] |
| Molyvan L | A thiaphosphomolybdate | Vanderbilt[2] |
| Lubrizol-5315 | Sulfurized cyclic carboxylate ester | Lubrizol[1] |
| Emcol TS 230 | Acid phosphate ester | Witco[3] |

[1]The Lubrizol Corporation, Wickliffe, Ohio, U.S.A.
[2]R. T. Vanderbilt Company, Inc., New York, N.Y., U.S.A.
[3]Witco Chemical Corp., Organics Division, Houston, Texas, U.S.A.

Mixtures of two or more of any of the afore-described functional additives can also be used.

Typically, a functionally effective amount of the functional additive is present in the aqueous systems of this invention. For example, if the functional additive is intended to serve primarily as a load-carrying agent, it is present in a load-carrying amount.

The aqueous systems of this invention often contain at least one inhibitor for corrosion of metals. These inhibitors can prevent corrosion of either ferrous or non-ferrous metals (e.g., copper, bronze, brass, titanium, aluminum and the like) or both. The inhibitor can be organic or inorganic in nature. Usually it is sufficiently soluble in water to provide a satisfactory inhibiting action though it can function as a corrosion inhibitor without dissolving in water, it need not be water-soluble. Many suitable inorganic inhibitors useful in the aqueous systems of the present invention are known to those skilled in the art. Included are those described in "Protective Coatings for Metals" by Burns and Bradley, Reinhold Publishing Corporation, Second Edition, Chapter 13, pages 596-605. This disclosure relative to inhibitors are hereby incorporated by reference. Specific examples of useful inorganic inhibitors include alkali metal nitrites, sodium di- and tri-polyphosphate, potassium and dipotassium phosphate, alkali metal borate and mixtures of the same. Many suitable organic inhibitors are known to those of skill in the art. Specific examples include hydrocarbyl amine and hydroxy-substituted hydrocarbyl amine neutralized acid compound, such as neutralized phosphates and hydrocarbyl phosphate esters, neutralized fatty acids (e.g., those having about 8 to about 22 carbon atoms), neutralized aromatic carboxylic acids (e.g., 4-tertiarybutyl benzoic acid), neutralized naphthenic acids and neutralized hydrocarbyl sulfonates. Mixed salt esters of alkylated succinimides are also useful. Particularly useful amines include the alkanol amines such as ethanol amine, diethanol amine, triethanol amine and the corresponding propanol amines. Mixtures of two or more of any of the afore-described corrosion inhibitors can also be used. The corrosion inhibitor is usually present in concentrations in which they are effective in inhibiting corrosion of metals with which the aqueous composition comes in contact.

The aqueous systems of the present invention can also include at least one shear stabilizing agent. Such shear stabilizing agents are especially useful where the system is intended to function as a hydraulic fluid. The shear stabilizing agent functions to make the viscosity of the aqueous system substantially independent of the shear applied to the fluid. Representative examples of such shear stabilizing agents include polyoxyalkylene polyols, particularly those where the alkylene group is an ethylene group, propylene group, or mixture of such groups and tetrasodium pyrophosphate. A specific shear stabilizing agent is available under the tradename Pluracol V-10 from BASF-Wyandotte Corporation, Wyandotte, Mich., U.S.A., Pluracol V-10 is a polyoxypropylene polyol having a viscosity at 38° C. of about 45,000 cSt. Typically, the shear stabilizing agent, when present, is present in a shear stabilizing amount.

Certain of the aqueous systems of the present invention (particularly those that are used in cutting or shaping of metal) can also contain at least one polyol with inverse solubility in water. Such polyols are those that become less soluble as the temperature of the water increases. They thus can function as surface lubricity agents during cutting or working operations since, as the liquid is heated as a result of friction between a metal workpiece and worktool, the polyol of inverse solubility "plates out" on the surface of the workpiece, thus improving its lubricity characteristics.

The aqueous systems of the present invention can also include at least one bacteriocide. Such bacteriocides are well known to those of skill in the art and specific examples can be found in the afore-mentioned McCutcheon publication "Functional Materials" under the heading "Antimicrobials" on pages 9–20 thereof. This disclosure is hereby incorporated by reference as it relates to suitable bacteriocides for use in the aqueous compositions or systems of this invention. Generally, these bacteriocides are watersoluble, at least to the extent to allow them to function as bacteriocides.

The aqueous systems of the present invention can also include such other materials as dyes, e.g., an acid green dye; water softeners, e.g., ethylene diamine tetraacetate sodium salt or nitrilo triacetic acid; odor masking agents, e.g., citronella, oil of lemon, and the like; and anti-foamants, such as the well-known silicone anti-foamant agents.

The aqueous systems of this invention may also include an anti-freeze additive where it is desired to use the composition at a low temperature. Materials such as ethylene glycol and analogous polyoxyalkylene polyols can be used as anti-freeze agents. Clearly, the amount used will depend on the degree of anti-freeze protection desired and will be known to those of ordinary skill in the art.

It should also be noted that many of the ingredients described above for use in making the aqueous systems of this invention are industrial products which exhibit or confer more than one property on such aqueous systems. Thus, a single ingredient can provide several functions thereby eliminating or reducing the need for some other additional ingredient. Thus, for example, an E.P. agent such as tributyl tin oxide can also function as a bactericide.

Illustrative aqueous concentrates within the scope of this invention are identified in Table II. Each of the concentrates identified below have application as cutting fluids or hydraulic fluids upon being diluted with water. The numerical values indicated in Table II are in parts by weight.

TABLE II

|  | A | B | C | D | E | F |
|---|---|---|---|---|---|---|
| Product of Example 2 | 450 | | | | | |
| Product of Example 4 | | 450 | | | | |
| Product of Example 6 | | | 150 | | 800 | |
| Product of Example 8 | | | | 600 | | 150 |
| Commercially available polyisobutenyl (950 mol. wt.) substituted succinic anhydride/diethylethanolamine reaction product | 780 | 780 | 166 | 767 | 682 | 166 |
| Diethanolamine | 51 | 51 | 10.9 | 50.2 | 44.7 | 10.9 |
| Diethylethanolamine | 120 | 120 | | 290 | 320 | |
| Triethylethanolamine | | | 540 | | | 540 |
| Unitol DT-40, a product of Union Camp, identified as distilled tall oil | 158 | 158 | 33.7 | 155.8 | 138.5 | 33.7 |
| Diluent oil | 61 | 61 | 179.2 | 827.1 | 735.1 | 179.2 |
| Grotan, a commercial bactericide available from Lehn & Fink, Div. of Sterling Drug | 60 | 60 | 54 | 80 | 80 | 54 |
| Foamban MS-30, a commercial anti-foaming agent available from Ultra Adhesives, Inc. | 30 | 30 | | | | |
| P & G Amide No. 27, commercial foam stabilizer identified as coconut fatty acid monoethanolamine available from Proctor & Gamble Co. | | | 42 | | | 42 |
| Pegosperse 100 S, commercial nonionic dispersing agent available from Glyco Chemicals, Inc. | | | 21 | 120 | 80 | 21 |
| Water | 1290 | 1290 | 1803 | 1120 | 1120 | 1803 |

EXAMPLE 10

20 parts of Concentrate C of Table II and 380 parts water are combined to form a water-based functional fluid.

EXAMPLE 11

20 parts of Concentrate E of Table II and 380 parts water are combined to form a water-based functional fluid.

EXAMPLE 12

2807 parts of Concentrate D of Table II are combined with 421 parts mineral oil to form a concentrate for use in metal working.

EXAMPLE 13

180 parts of the concentrate formed in Example 12 and 3420 parts water are combined to form a water-based functional fluid.

EXAMPLE 14

20 parts of Concentrate F from Table II and 380 parts water are combined to form a water-based functional fluid.

EXAMPLE 15

The acute oral toxicity of the product of Example 2 in rats is measured using the following procedure. Outbred Sprague-Dawley rats, weighing 200-300 grams, are used. The animals are obtained from Ace Animals, Inc., Boyertown, PA., a U.S.D.A. licensed animal dealer. The animals are housed and maintained in accordance with standards set forth in the Guide for the Care and Use of Laboratory Animals (DHEW Publication No. 80-23). The rats are acclimated to the laboratory for an appropriate time prior to dosing. Each cage is identified with a cage card displaying the number of animals, sex, project number, date dosed, dose level and responsible technician's initials. Husbandry conditions are as follows:
Temperature: 65° F.-73° F.
Relative Humidity: 45%-55%
Light: 12 hour light/dark cycle
Diet: Wayne Lab-Blox and tap water are provided ad libitum.
Caging: Stainless steel with elevated wire mesh flooring 5 rats/cage by sex The product of Example 2 is dosed as a 50% w/v mixture in corn oil. Two groups of ten (5 male & 5 female) albino rats are deprived of food, but not water overnight prior to dosing. Each animal is weighed and dosed by direct administration of the experimental material into the stomach by gavage. The following dosage levels are administered: 2.0 g/kg, 5.0 g/kg. Following administration, the animals are allowed food and water ad libitum for the 14-day observation period during which time the rats are observed for signs of toxicity and mortality. Animals are observed frequently on the day of dosage, and twice per day thereafter (morning and afternoon). Individual weights are recorded on the day of dosage, and average group weights are recorded at 7 and 14 days after dosing. A gross necropsy is performed on all animals that are found dead during the study and on the remaining animals at the conclusion of the study. The product of Example 2 when studied in male and female albino rats has an acute oral $LD_{50}$ greater than 2.0 g/kg, but less than 5.0 g/kg.

EXAMPLE 16

The product of Example 4 is tested using the procedure of Example 15 with the result being an $LD_{50}$ greater than 5.0 g/kg.

EXAMPLE 17

The primary skin irritation in the product of Example 2 may produce when applied to the intact and abraded skin or albino rabbits is measured using the following procedure.

New Zealand White rabbits are used for this study. The animals are obtained from Ace Animals, Inc., Boyertown, Pa., a U.S.D.A. licensed animal dealer. The animals are housed and maintained in accordance with standards set forth in the Guide for the Care and Use of Laboratory Animals (DHEW Publication No. 80-23). The rabbits are acclimated to the laboratory for an appropriate time prior to dosing. The animals are individually identified by an ear tag. Each cage is identified with a cage card displaying the animal number, project number, date dosed, dose level and responsible technician's initials. Husbandry conditions are as follows:
Temperature: 60° F.-75° F.
Relative Humidity: 40%-45%
Light: 12 hour light/dark cycle
Diet: Wayne 15% Rabbit Ration and tap water were provided ad libitum.
Caging: Stainless steel with elevated wire mesh flooring, 1 rabbit/cage Prior to application, the backs of six rabbits are clipped free of hair. Two sites on each rabbit are used. One site is left intact and the other is abraded sufficiently deep to penetrate the stratum corneum but not enter the derma to produce bleeding. A 0.5 ml portion of the product of Example 2 is applied to one abraded and intact skin site on each rabbit. Gauze patches are placed over the treated areas and an impervious material is wrapped snugly around the trunks of the animals to hold the patches in place. The wrapping is removed at the end of the 24-hour period, the sites wiped but not washed, and the treated areas examined. Readings are also made at 72-hours. The Draize method of scsoring is employed. The irritation index is 6.17.

EXAMPLE 18

The product of Example 4 is tested using the procedure of Example 17 with the result being an irritation index of 0.7.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

I claim:
1. A composition comprising water and dispersed in said water the reaction product of
(A) at least one carboxylic acid acylating agent;
(B) at least one amine characterized by the presence within its structure of at least one HN< group; and
(C) at least one phosphorus-containing acid of the formula

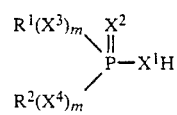

wherein each $X^1$, $X^2$, $X^3$ and $X^4$ is independently oxygen or sulfur, each m is zero or one, and each $R^1$ and $R^2$ is independently a hydrocarbyl group.

2. The composition of claim 1 wherein the ratio of components (A) and (C) to component (B) is at least one-half an equivalent of each of components (A) and (C) per mole of component (B).

3. The composition of claim 1 wherein component (B) has about 5 HN< groups per mole, and from about 0.5 to about 4.5 equivalents of each of components (A) and (C) are reacted with component (B).

4. The composition of claim 1 wherein component (A) is (i) one or more lower molecular weight carboxylic acid acylating agents of from one to less than about 18 carbon atoms, (ii) one or more higher molecular weight hydrocarbyl-substituted carboxylic acid acylating agents, the hydrocarbyl-substituent having an average of at least about 12 carbon atoms, or (iii) a mixture of (i) and (ii).

5. The composition of claim 1 wherein component (A) is one or more lower molecular weight carboxylic acid of from 1 to about 18 carbon atoms, or the anhydride, lower alkyl ester or acid halide of said acid.

6. The composition of claim 1 wherein component (A) is a fatty acid of from 10 to about 18 carbon atoms.

7. The composition of claim 1 wherein component (A) has the formula

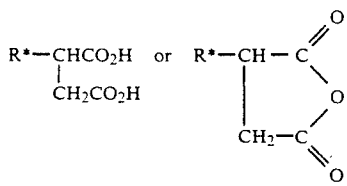

wherein R* is a $C_1$ to about a $C_{10}$ hydrocarbyl group.

8. The composition of claim 1 wherein component (A) is one or more hydrocarbyl-substituted carboxylic acid acylating agents, the hydrocarbyl substituent having an average of at least about 12 carbon atoms.

9. The composition of claim 8 wherein said hydrocarbyl substituent has an average of at least about 18 carbon atoms.

10. The composition of claim 8 wherein said hydrocarbyl substituent has an average of at least about 30 carbon atoms.

11. The composition of claim 8 wherein said hydrocarbyl substituent has an average of at least about 50 carbon atoms.

12. The composition of claim 1 wherein component (A) has the formula

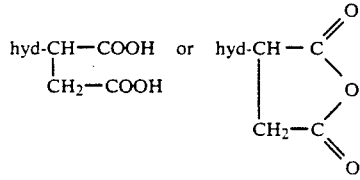

wherein hyd is a hydrocarbyl group having an average of at least about 12 carbon atoms.

13. The composition of claim 12 wherein hyd is a hydrocarbyl group having an average of at least about 18 carbon atoms.

14. The composition of claim 12 wherein hyd is a hydrocarbyl group having an average of at least about 30 carbon atoms.

15. The composition of claim 12 wherein hyd is a hydrocarbyl group having an average of at least about 50 carbon atoms.

16. The composition of claim 8 wherein said hydrocarbyl substituent as derived from a polyisobutene.

17. The composition of claim 12 wherein hyd is derived from a polyisobutene.

18. The composition of claim 1 wherein component (B) is a monoamine or a polyamine.

19. The composition of claim 1 wherein component (B) is hydrazine or a subsituted hydrazine.

20. The composition of claim 1 wherein component (B) is an aliphatic, cycloaliphatic or aromatic monoamine or polyamine.

21. The composition of claim 1 wherein component (B) is a monoamine of up to about 40 carbon atoms.

22. The composition of claim 1 wherein component (B) is a hydroxy amine.

23. The composition of claim 1 wherein component (B) is an aminosulfonic acid.

24. The composition of claim 1 wherein component (B) is a hydrocarbyl polyamine prepared by reacting a chlorinated polyolefin having a molecular weight of at least about 400 with ammonia or amine.

25. The composition of claim 1 wherein component (B) is a branched polyalkylene polyamine.

26. The composition of claim 1 wherein component (B) is a polyoxyalkylene diamine or a polyoxyalkylene triamine, said diamine and said triamine having an average molecular weight of at least about 200.

27. The composition of claim 1 wherein component (B) is an alkylene polyamine of the formula

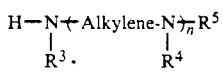

wherein n is an integer from 1 to about 10; each $R^3$, $R^4$ and $R^5$ is independently a hydrogen atom, a hydrocarbyl group or a hydroxy-substituted hydrocarbyl group having an average up to about 40 carbon atoms, and the Alkylene group has an average of from 1 to about 10 carbon atoms.

28. The composition of claim 27 wherein each $R^3$, $R^4$ and $R^5$ independently has an average of up to about 30 carbon atoms.

29. The composition of claim 27 wherein each $R^3$, $R^4$ and $R^5$ independently has an average of from 1 to about 10 carbon atoms.

30. The composition of claim 27 wherein the Alkylene group has an average of from 1 to about 10 carbon atoms.

31. The composition of claim 27 wherein the Alkylene group has an average of from about 2 to about 6 carbon atoms.

32. The composition of claim 27 wherein the Alkylene group is ethylene or propylene.

33. The composition of claim 27 wherein n ranges on average from about 2 to about 7.

34. The composition of claim 1 wherein component (B) is a polyalkylene polyamine.

35. The composition of claim 1 wherein component (B) is a tetraalkylene pentamine.

36. The composition of claim 1 wherein component (B) is tetraethylene pentamine.

37. The composition of claim 1 wherein each $R^1$ and $R^2$ is independently a hydrocarbyl group of an average of about 1 to about 50 carbon atoms.

38. The composition of claim 1 wherein each $R^1$ and $R^2$ is independently a hydrocarbyl group of an average of about 1 to about 30 carbon atoms.

39. The composition of claim 1 wherein each $R^1$ and $R^2$ is independently a hydrocarbyl group of an average of about 3 to about 18 carbon atoms.

40. The composition of claim 1 wherein each $R^1$ and $R^2$ is independently a hydrocarbyl group of about 4 to about 8 carbon atoms.

41. The composition of claim 1 wherein component (C) has the formula

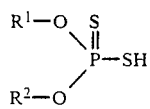

42. The composition of claim 1 wherein component (C) is a di-(alkyl)phosphorodithioic acid wherein each alkyl has independently from about 4 to about 8 carbons.

43. The composition of claim 1 wherein component (C) is O,O-di(isooctyl) phosphorodithioic acid.

44. A composition comprising the reaction product of (a) at least one polyisobutene-substituted succinic acid or anhydride, (b) at least one tetraalkylene pentamine, and (c) at least one phosphorodithioic acid, the ratio of equivalents of each of (a) and (c) to moles of (b) being in the range of about 0.5:1 to about 4.5:1.

45. An aqueous concentrate comprising at least about 25% water and the composition of any one of claims 1.

46. A water-based functional fluid comprising a major amount of water and a minor E.P., anti-wear and/or load-carrying amount of the composition of any one of claims 1.

* * * * *